(12) United States Patent
Reynard et al.

(10) Patent No.: US 11,331,164 B2
(45) Date of Patent: May 17, 2022

(54) METHOD AND APPARATUS FOR DENTAL VIRTUAL MODEL BASE

(71) Applicant: CARESTREAM HEALTH, INC., Rochester, NY (US)

(72) Inventors: Delphine Reynard, Montreuil (FR); Sebastien Henry, Arcueil (FR); Sabrina Capron-Richard, Noisiel (FR)

(\*) Notice: Subject to any disclaimer, the term of this patent is extended or adjusted under 35 U.S.C. 154(b) by 0 days.

(21) Appl. No.: 15/326,252

(22) PCT Filed: Aug. 28, 2015

(86) PCT No.: PCT/IB2015/001840
§ 371 (c)(1),
(2) Date: Jan. 13, 2017

(87) PCT Pub. No.: WO2016/030754
PCT Pub. Date: Mar. 3, 2016

(65) Prior Publication Data
US 2017/0202639 A1  Jul. 20, 2017

Related U.S. Application Data

(60) Provisional application No. 62/043,732, filed on Aug. 29, 2014.

(51) Int. Cl.
| | |
|---|---|
| *A61C 3/00* | (2006.01) |
| *A61C 7/00* | (2006.01) |
| *A61C 9/00* | (2006.01) |
| *A61B 1/06* | (2006.01) |
| *A61B 1/24* | (2006.01) |
| *A61B 6/14* | (2006.01) |

(52) U.S. Cl.
CPC .............. *A61C 7/002* (2013.01); *A61B 1/063* (2013.01); *A61B 1/24* (2013.01); *A61B 6/14* (2013.01); *A61C 9/006* (2013.01); *A61C 9/0046* (2013.01)

(58) Field of Classification Search
CPC ....... A61C 7/002; A61C 9/0046; A61C 9/006; A61C 13/0004; A61B 1/24; A61B 1/063; A61B 6/14
See application file for complete search history.

(56) References Cited

U.S. PATENT DOCUMENTS

| 6,767,208 B2 * | 7/2004 | Kaza ...................... A61C 7/002 |
| | | 433/24 |
| 7,220,124 B2 * | 5/2007 | Taub .................... A61C 11/001 |
| | | 433/213 |

(Continued)

OTHER PUBLICATIONS

International Search Report dated Dec. 23, 2015 for International Application No. PCT/IB2015/001840, 2 pages.

*Primary Examiner* — Nicholas D Lucchesi

(57) ABSTRACT

Method and/or apparatus embodiments can provide a virtual orthodontic base, adapted to each virtual 3D dental model of the teeth (e.g., upper and lower jaw). The virtual orthodontic base should match each 3D model (e.g., size), conform to prescribed dimensional requirements and still be rapidly calculated. The 3D virtual teeth model can be provided or reconstructed (e.g., from a laser scanning, intra oral camera scanning or x-ray scan of a plaster, a negative impression (e.g., alginate or silicon) of a patient's dentition or directly from the patient's mouth).

11 Claims, 16 Drawing Sheets

(56) References Cited

U.S. PATENT DOCUMENTS

| | | | |
|---|---|---|---|
| 7,362,890 B2 * | 4/2008 | Scharlack | A61C 13/0004 382/128 |
| 7,702,492 B2 * | 4/2010 | Marshall | G06T 17/00 433/68 |
| 7,716,024 B2 * | 5/2010 | Hultgren | G06T 19/20 703/6 |
| 7,810,249 B2 * | 10/2010 | Matsuda | A61C 13/0004 33/513 |
| 7,824,346 B2 * | 11/2010 | Marshall | G16H 50/50 600/590 |
| 7,899,221 B2 * | 3/2011 | Weber | A61C 13/0004 382/128 |
| 8,026,943 B2 * | 9/2011 | Weber | A61C 13/0004 348/77 |
| 8,366,445 B2 * | 2/2013 | Vuillemot | A61C 13/0004 433/213 |
| 8,491,306 B2 * | 7/2013 | Raby | A61C 7/146 433/213 |
| 8,753,114 B2 * | 6/2014 | Vuillemot | A61C 13/0004 433/36 |
| 8,995,732 B2 * | 3/2015 | Kaza | A61C 7/002 382/128 |
| 9,326,834 B2 * | 5/2016 | Morales | A61C 13/01 |
| 9,642,686 B1 * | 5/2017 | Kalman | A61C 9/0053 |
| 9,687,327 B2 * | 6/2017 | Prestipino | A61C 13/34 |
| 9,707,061 B2 * | 7/2017 | Morales | A61C 13/34 |
| 9,795,463 B1 * | 10/2017 | Wallace | A61C 13/0001 |
| 9,801,700 B1 * | 10/2017 | Liberkowski | A61C 13/01 |
| 9,848,965 B2 * | 12/2017 | Kim | A61C 1/084 |
| 10,111,728 B2 * | 10/2018 | Ripoche | A61C 1/084 |
| 10,166,091 B2 * | 1/2019 | Cowburn | A61C 19/04 |
| 10,182,893 B2 * | 1/2019 | Baaske | A61C 13/00 |
| 2002/0081554 A1 | 6/2002 | Marshall et al. | |
| 2012/0276502 A1 | 11/2012 | Marshall | |
| 2014/0186796 A1 | 7/2014 | Suttin | |

* cited by examiner

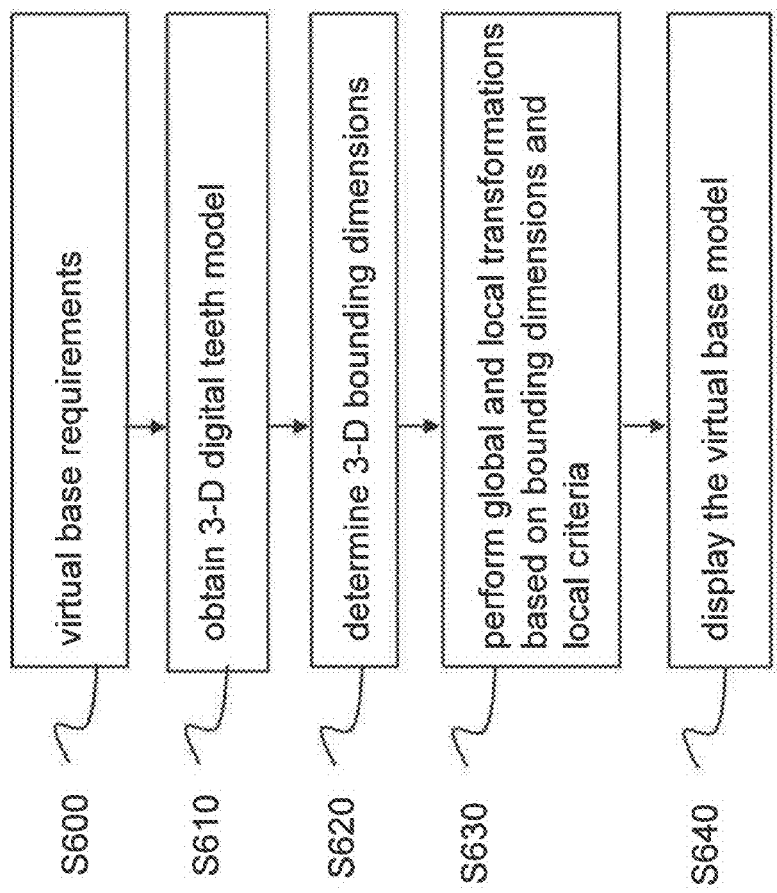

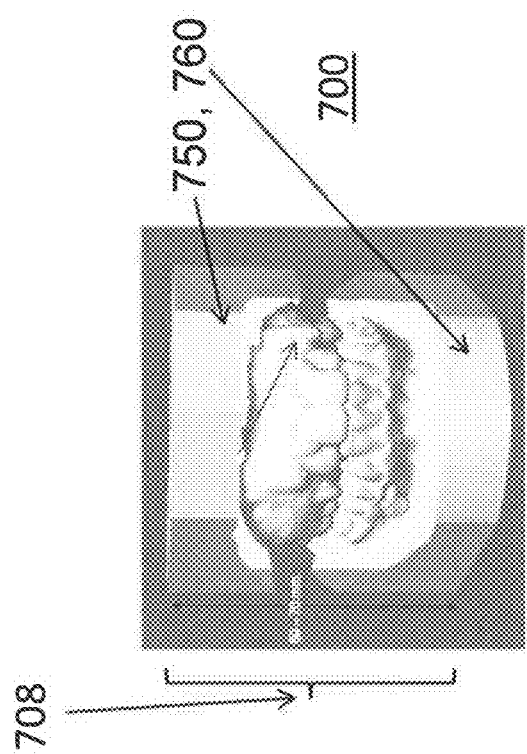

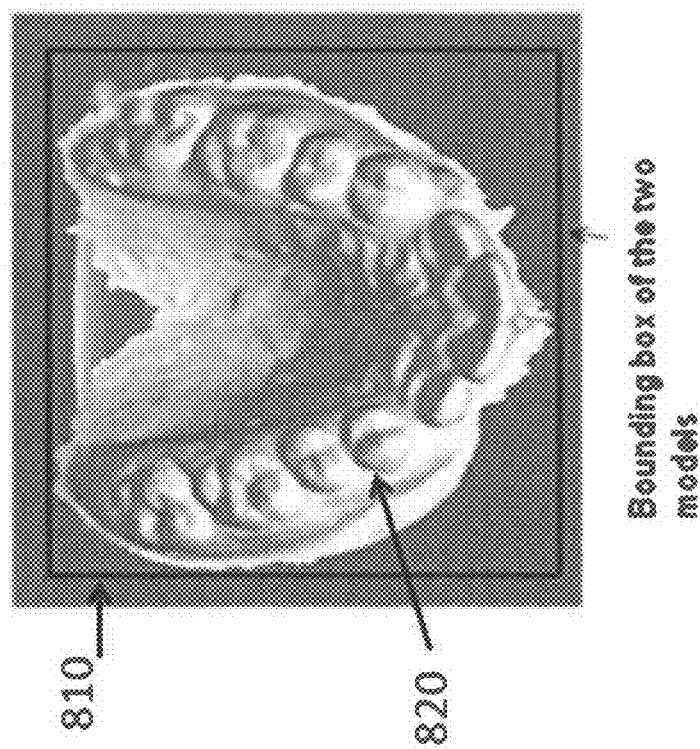

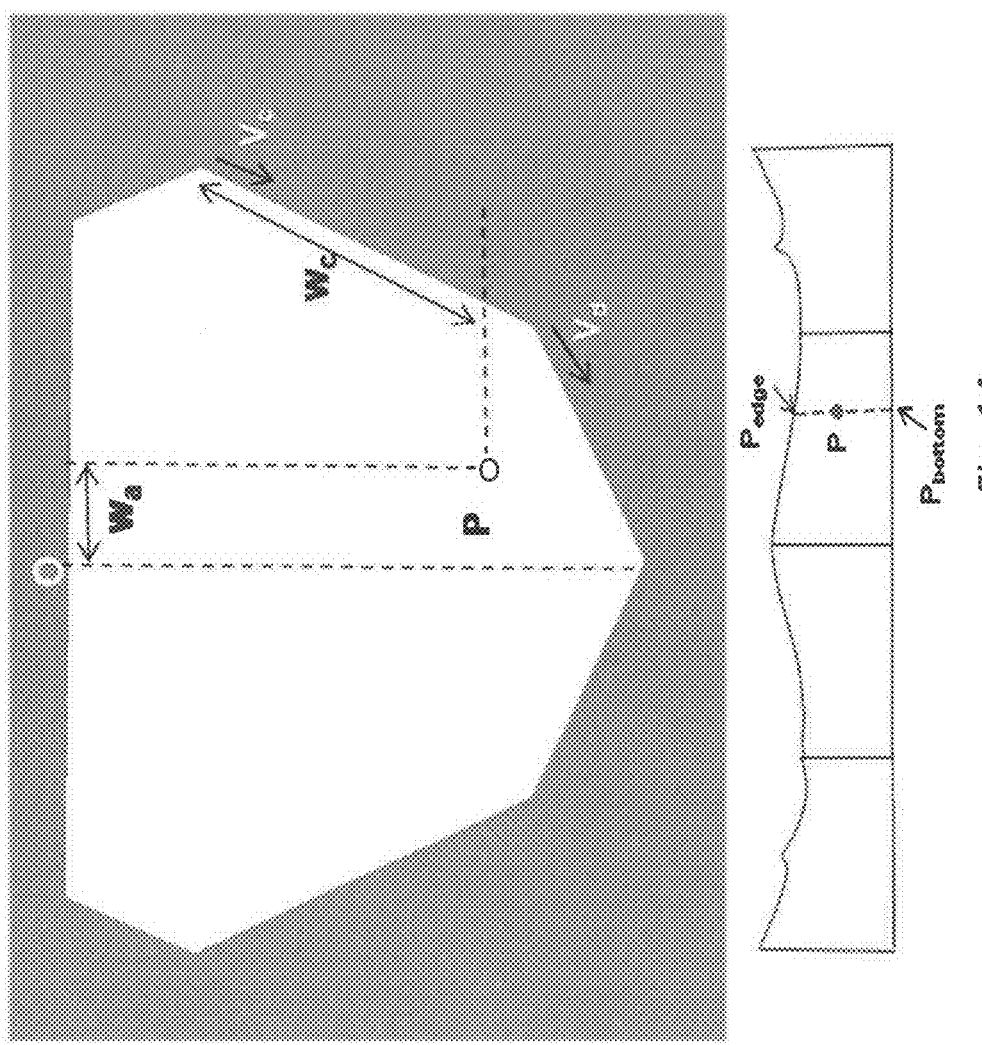

METHOD AND APPARATUS FOR DENTAL VIRTUAL MODEL BASE

CROSS REFERENCE TO RELATED APPLICATIONS

This application claims the benefit of and is a U.S. National Phase filing of PCT Application PCT/IB15/01840 filed Aug. 28, 2015 entitled "METHOD AND APPARATUS FOR DENTAL VIRTUAL MODEL BASE", in the name of Delphine Reynard et al, which claims benefit of U.S. Provisional application U.S. Ser. No. 62/043,732, provisionally filed on Aug. 29, 2014, entitled "VIRTUAL ORTHODONTIC BASE", in the name of Delphine Reynard et al, all of which are incorporated herein in their entirety.

TECHNICAL FIELD

The disclosure relates generally to the field of dental diagnostic imaging and more particularly relates to three-dimensional imaging of patient dentition and three-dimensional bases for positioning three-dimensional teeth models.

BACKGROUND

A virtual teeth model is received, provided, or reconstructed (e.g., from a laser scanning or intra oral camera scanning of a plaster, a negative impression (e.g., alginate or silicon) of a patient's dentition or directly the patient's mouth). The virtual teeth model can also be obtained from an x-ray scan of a plaster model or a negative impression of the patient's teeth. The virtual models are positioned on a virtual base. There is, however, a need for improved methods and/or apparatus for generation of virtual teeth base models.

SUMMARY OF THE INVENTION

An aspect of this application is to advance the art of medical diagnostic treatment, particularly for dental applications.

Another aspect of this application is to address, in whole or in part, at least the foregoing and other deficiencies in the related art.

It is another aspect of the application to provide, in whole or in part, at least the advantages described herein.

An advantage offered by apparatus and/or method embodiments of the application relates to repeatable, consistent, and/or accurate positioning of a dental virtual model.

Another advantage offered by apparatus and/or method embodiments of the application relates to virtual definition of a base of a dental virtual model.

Another advantage offered by apparatus and/or method embodiments of the application relates to consistent positioning of virtual models of the teeth of a patient in accordance with dental regulatory requirement standards.

According to one aspect of the disclosure, there is provided a method for generating a digital model base from a digital model of a patient's dentition, that can include obtaining a plurality of prescribed dimensions of a selected virtual base type; obtaining a 3-D digital model of the patient's dentition; determining a bounding dimensions of the 3-D digital model of the patient's dentition; automatically forming the digital model base from the plurality of prescribed dimensions and the bounding dimensions of the 3-D digital model of the patient's dentition; and displaying, storing or transmitting the at least one virtual model base with the 3-D digital model of the patient's dentition.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting x-ray system components, for example, are not shown in the drawings in order to simplify description.

FIG. 6 is a logic flow diagram that shows an exemplary method embodiment for virtual teeth base generation according to the application.

FIGS. 7a-7e are diagram that show a perspective view, top view and side views of an exemplary virtual dental base model embodiment.

FIG. 8 is a diagram that shows exemplary boundary dimensions to surround a 3-D teeth model.

FIG. 14 is a diagram that illustrates local movements along an exemplary virtual base model embodiment.

DESCRIPTION OF EXEMPLARY EMBODIMENTS

Figure 1:
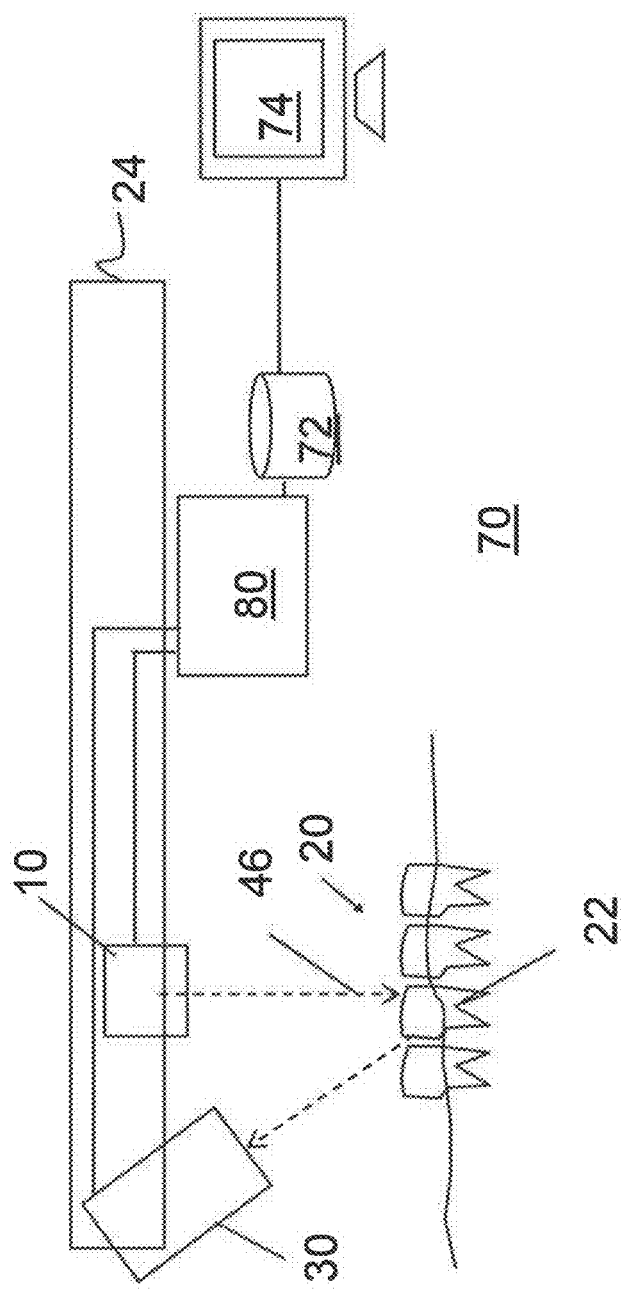
FIG. 1 is a schematic diagram that shows components of an imaging apparatus for surface contour imaging of a patient's teeth and related structures.

The following is a description of exemplary embodiments, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

The term "in signal communication" as used in the application means that two or more devices and/or components are capable of communicating with each other via signals that travel over some type of signal path. Signal communication may be wired or wireless. The signals may be communication, power, data, or energy signals which may communicate information, power, and/or energy from a first device and/or component to a second device and/or component along a signal path between the first device and/or component and second device and/or component. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional or volume images and a pixel for 2-dimensional (2-D) images. For the purposes of the description herein, the terms voxel and pixel can generally be considered equivalent, describing an image elemental datum that is capable of having a range of numerical values. Voxels and pixels have attributes of both spatial location and image data code value.

"Patterned light" is used to indicate light that has a predetermined spatial pattern, such that the light has one or more features such as one or more discernible parallel lines, curves, a grid or checkerboard pattern, or other features having areas of light separated by areas without illumination. In the context of the present disclosure, the phrases "patterned light" and "structured light" are considered to be equivalent, both used to identify the light that is projected onto the head of the patient in order to derive contour image data.

In the context of the present disclosure, the terms "viewer", "operator", and "user" are considered to be equivalent and refer to the viewing practitioner, technician, or other person who views and manipulates a contour image that is formed from a combination of multiple structured light images on a display monitor.

A "viewer instruction", "operator instruction", or "operator command" can be obtained from explicit commands entered by the viewer or may be implicitly obtained or derived based on some other user action, such as making an equipment setting, for example. With respect to entries entered on an operator interface, such as an interface using a display monitor and keyboard, for example, the terms "command" and "instruction" may be used interchangeably to refer to an operator entry.

In the context of the present disclosure, a single projected line of light is considered a "one dimensional" pattern, since the line has an almost negligible width, such as when projected from a line laser, and has a length that is its predominant dimension. Two or more of such lines projected side by side, either simultaneously or in a scanned arrangement, provide a two-dimensional pattern. In exemplary embodiments, lines of light can be linear, curved or three-dimensional.

The terms "3-D model", "point cloud", "3-D surface", and "mesh" may be used synonymously in the context of the present disclosure. The dense point cloud is formed using techniques familiar to those skilled in the volume imaging arts for forming a point cloud and relates generally to methods that identify, from the point cloud, vertex points corresponding to surface features. The dense point cloud is thus generated using the reconstructed contour data from one or more reflectance images. Dense point cloud information serves as the basis for a polygon model at high density for the teeth and aura surface.

Apparatus and/or method embodiments according to the application aim at virtual definition of a base of a dental virtual model for facilitating a repeatable, accurate and rapid orientation of a virtual dental model to the base. Certain exemplary embodiments can provide automatic formation of digital model bases from a plurality of prescribed dimensions and bounding dimensions of a 3-D digital model of the patient's dentition. One exemplary use of virtual dental models is for virtual storage purposes in orthodontic treatment.

A virtual teeth model is received, provided, or reconstructed (e.g., from a laser scanning or intra oral camera scanning of a plaster, a negative impression (e.g., alginate or silicon) of a patient's dentition or directly the patient's mouth). The virtual teeth model can also be obtained from an x-ray scan of a plaster model or a negative impression of the patient's teeth. Thus, the virtual teeth models can be obtained using intraoral or extraoral scanning devices/methods. The virtual teeth models can be positioned on a virtual base or virtual base model. One exemplary use of this virtual teeth model is for virtual storage purposes in orthodontic treatment.

In one embodiment, a virtual teeth model of a patient's dentition can be obtained from an intraoral scanner.

FIG. 1 is a schematic diagram showing an imaging apparatus 70 for projecting and imaging using structured light patterns 46. Imaging apparatus 70 uses a handheld camera 24 for image acquisition according to an embodiment of the present disclosure. A control logic processor 80, or other type of computer that may be part of camera 24 controls the operation of an illumination array 10 that generates the structured light and controls operation of an imaging sensor array 30. Image data from surface 20, such as from a tooth 22, is obtained from imaging sensor array 30 and stored in a memory 72. Control logic processor 80, in signal communication with camera 24 components that acquire the image, can process the received image data and stores the mapping in memory 72. The resulting image from memory 72 is then optionally rendered and displayed on a display 74. Memory 72 may also include a display buffer for temporarily storing display 74 image content. Control logic processor 80 can be part of a standalone computer or workstation with a separate display and user input functions. Control logic processor 80 can be remotely located relative to a camera 24.

In fringe projection imaging of a surface, a pattern of lines is projected from illumination array 10 toward the surface of an object from a given angle. The projected pattern from the surface is then viewed from another angle as a contour image, taking advantage of triangulation in order to analyze surface information based on the appearance of contour lines. Phase shifting, in which the projected pattern is incrementally shifted spatially for obtaining additional measurements at the new locations, is typically applied as part of fringe projection imaging, used in order to complete the contour mapping of the surface and to increase overall resolution in the contour image.

Figure 2:
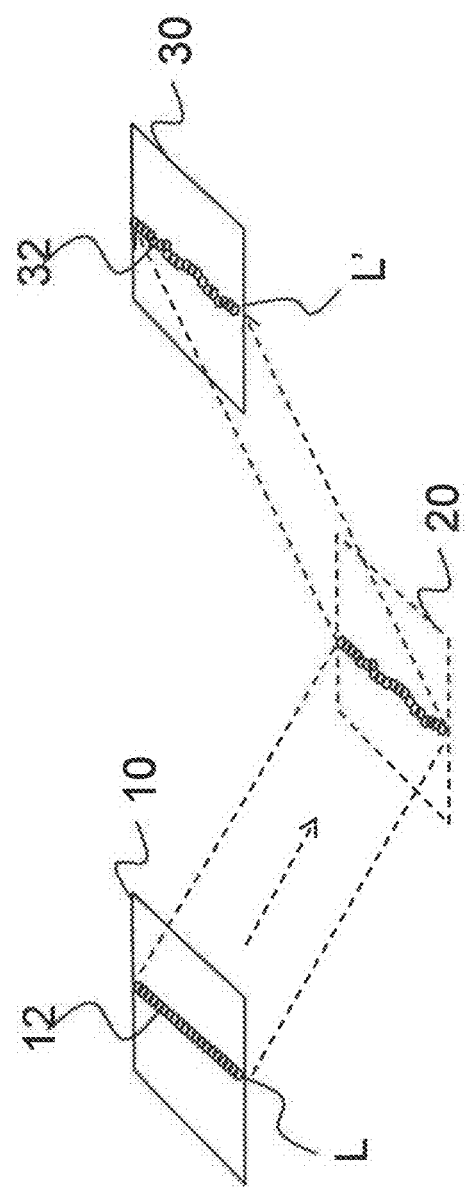
FIG. 2 shows schematically how patterned light is used for obtaining surface contour information using a handheld camera or other portable imaging device.

The schematic diagram of FIG. 2 shows, with the example of a single line of light L, how patterned light is used for obtaining surface contour information using a handheld camera or other portable imaging device. A mapping is obtained as an illumination array 10 directs a pattern of light onto a surface 20 and a corresponding image of a line L' is formed on an imaging sensor array 30. Each pixel 32 on imaging sensor array 30 maps to a corresponding pixel 12 on illumination array 10 according to modulation by surface 20. Shifts in pixel position, as represented in FIG. 2, yield useful information about the contour of surface 20. It can be appreciated that the basic pattern shown in FIG. 2 can be implemented in a number of ways, using a variety of illumination sources and sequences and using one or more different types of sensor arrays 30. Illumination array 10 can utilize any of a number of types of arrays used for light modulation, such as a liquid crystal array or digital micromirror array, such as that provided using the Digital Light Processor or DLP device from Texas Instruments, Dallas, Tex. This type of spatial light modulator is used in the illumination path to change the light pattern as needed for the mapping sequence.

By projecting and capturing images that show structured light patterns that duplicate the arrangement shown in FIGS. 1 and 2 multiple times, the image of the contour line on the camera simultaneously locates a number of surface points of the imaged object. This can speed the process of gathering many sample points, while the plane of light (and usually also the receiving camera) is laterally moved in order to "paint" some or all of the exterior surface of the object with the plane of light.

Figure 3:
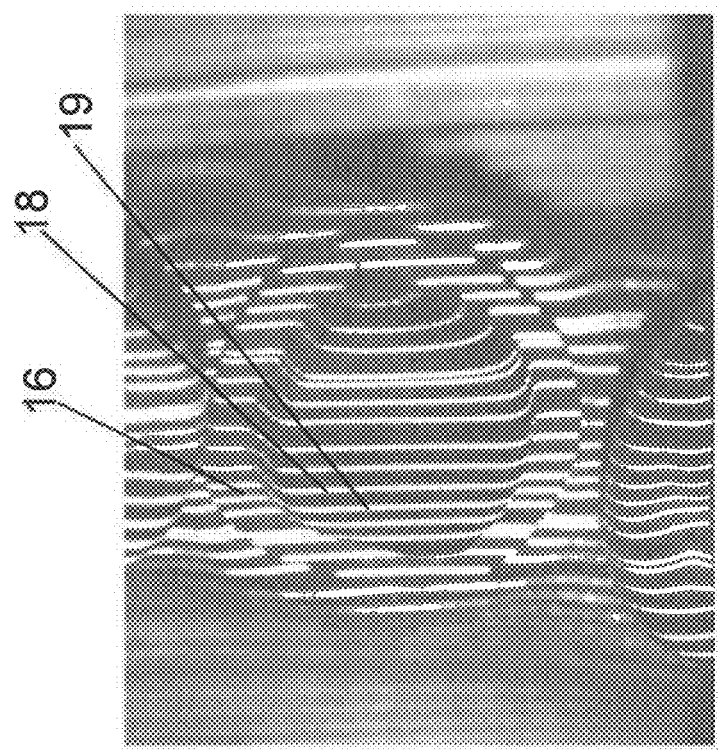
FIG. 3 shows an example of surface imaging using a pattern with multiple lines of light.

FIG. 3 shows surface imaging using a pattern with multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult to determine whether line segment 16 is from the same line of illumination as line segment 18 or adjacent line segment 19.

Figure 4:
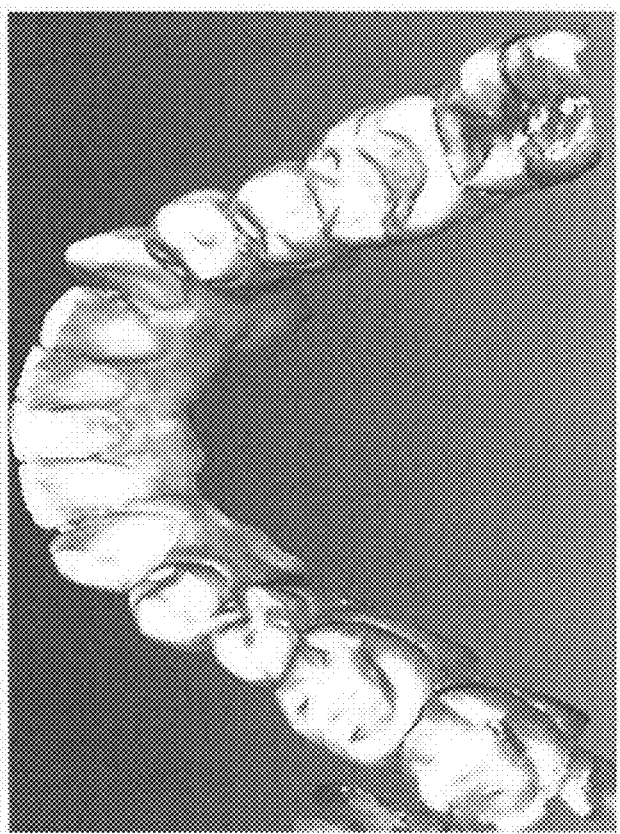
FIG. 4 shows a point cloud generated from structured light imaging, such as that shown in FIG. 3.

By knowing the instantaneous position of the camera and the instantaneous position of the line of light within an object-relative coordinate system when the image was acquired, a computer and software can use triangulation methods to compute the coordinates of numerous illuminated surface points. As the plane is moved to intersect eventually with some or all of the surface of the object, the coordinates of an increasing number of points are accumulated. As a result of this image acquisition, a point cloud of vertex points or vertices can be identified and used to represent the extent of a surface within a volume. By way of example, FIG. 4 shows a dense point cloud 50 generated from a structured light imaging apparatus, CS 3500 3-D camera made by Carestream Heath, Inc., Rochester N.Y., USA, using results from patterned illumination such as that shown in FIG. 3. The point cloud 50 models physical location of sampled points on tooth surfaces and other intraoral surfaces or, more generally, of surfaces of a real-world object. Variable resolution can be obtained. The example of FIG. 4 shows an exemplary 100 micron resolution. The points in the point cloud represent actual, measured points on the three dimensional surface of an object.

The surface structure can be approximated from the point cloud representation by forming a polygon mesh, in which adjacent vertices are connected by line segments. For a vertex, its adjacent vertices are those vertices closest to the vertex in terms of Euclidean distance.

Figure 5:
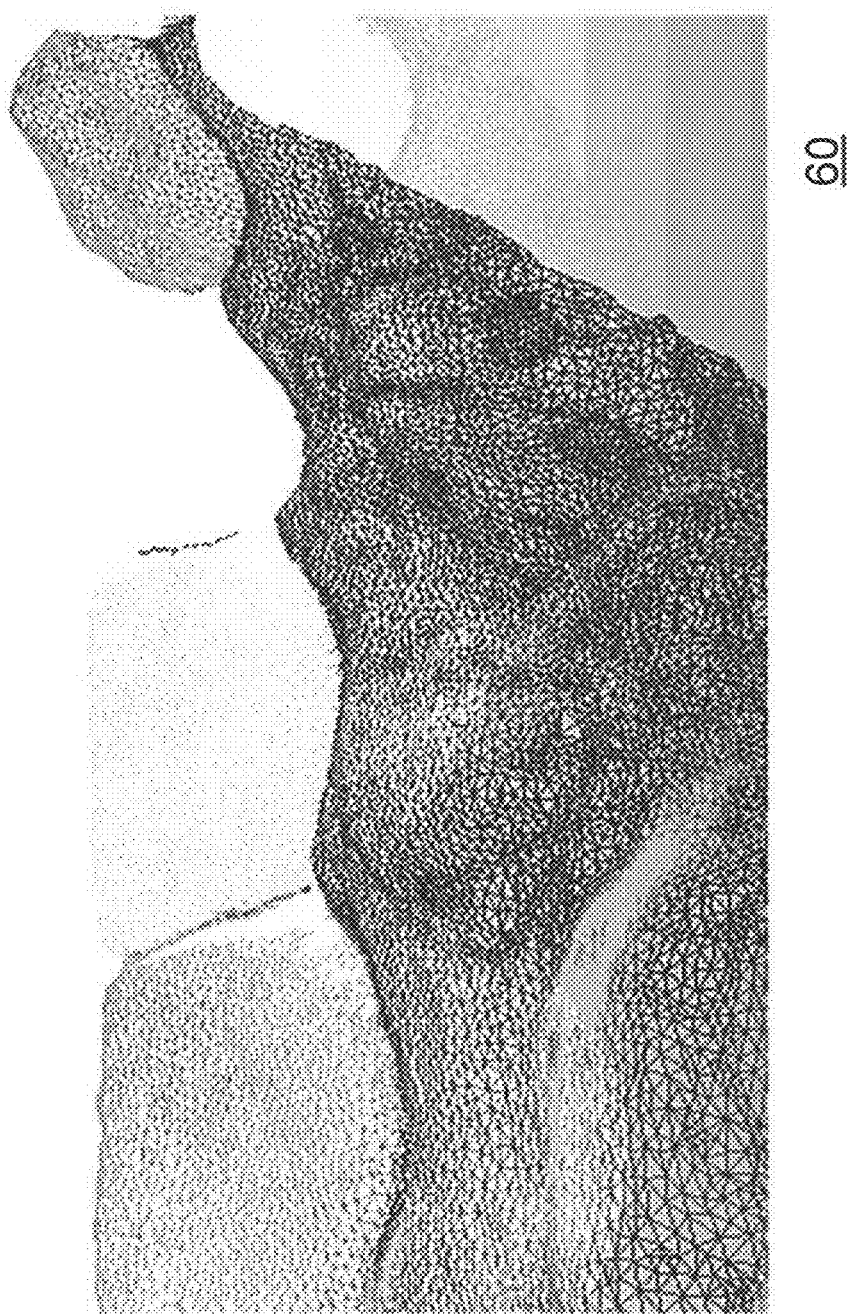
FIG. 5 shows a polygon mesh in the simple form of a triangular mesh.

By way of example, FIG. 5 shows a 3-D polygon mesh model 60 (e.g., of a patient's dentition) in the simple form of a triangular mesh. A triangular mesh forms a basic mesh structure that can be generated from a point cloud and used as a digital model to represent a 3-D object by its approximate surface shape, in the form of triangular plane segments sharing adjacent boundaries. Methods/apparatus for forming a polygon mesh model, such as a triangular mesh or more complex mesh structure, are well known to those skilled in the contour imaging arts.

The logic flow diagram of FIG. 6 shows an exemplary method embodiment for virtual teeth base generation (e.g., orthodontic base models) according to the present disclosure. Starting from the reconstructed 3D virtual teeth model, certain exemplary method and/or apparatus embodiments provide a virtual treatment of a base of this virtual teeth model (virtual reconstructed teeth model). The virtual teeth model can be or is required to be shown on a virtual orthodontic base, with the consideration or respect of the regulatory requirements (for example, the American Board of Orthodontics (ABO) policy). Certain exemplary virtual base embodiments herein are adapted to at least the size of the virtual teeth model.

As shown in FIG. 6, in a virtual base requirements step S600, a plurality of virtual base requirements of rules can be obtained. Some exemplary virtual base embodiments herein respect at least the virtual orthodontic base regulatory requirements of the American Board of Orthodontics (ABO). For example, certain exemplary virtual base embodiments herein respect at least the following rules:

The length of the oblique faces on the rear corner of the base (b) is 13.0 mm

The indicated angles are 65.0° (e.g., the direction of all the faces are imposed by the regulatory agencies)

The minimal height of the base is 13.0 mm

The distance between a maxillary base and a mandibular base is comprised between 60.0 and 70.0 mm.

Embodiments of the application are not intended to be so limited, however, since in alternative embodiments, additional rules, different rules can be followed by such an exemplary dental virtual base embodiment.

FIG. 7a is a diagram that shows a perspective view of an exemplary virtual dental base model embodiment (e.g., maxillary arch and/or mandibular arch) according to the application. As shown in FIG. 7a, an exemplary virtual dental base model embodiment 700 can include upper and/or lower portions (e.g., maxillary arch and/or mandibular arch) according to the application. A first distance 707 between a lower portion 750 and an upper portions 760 is preferably between a first prescribed range so a height of the model 700 is between a prescribed height range 708.

Figures 7B, 7C:
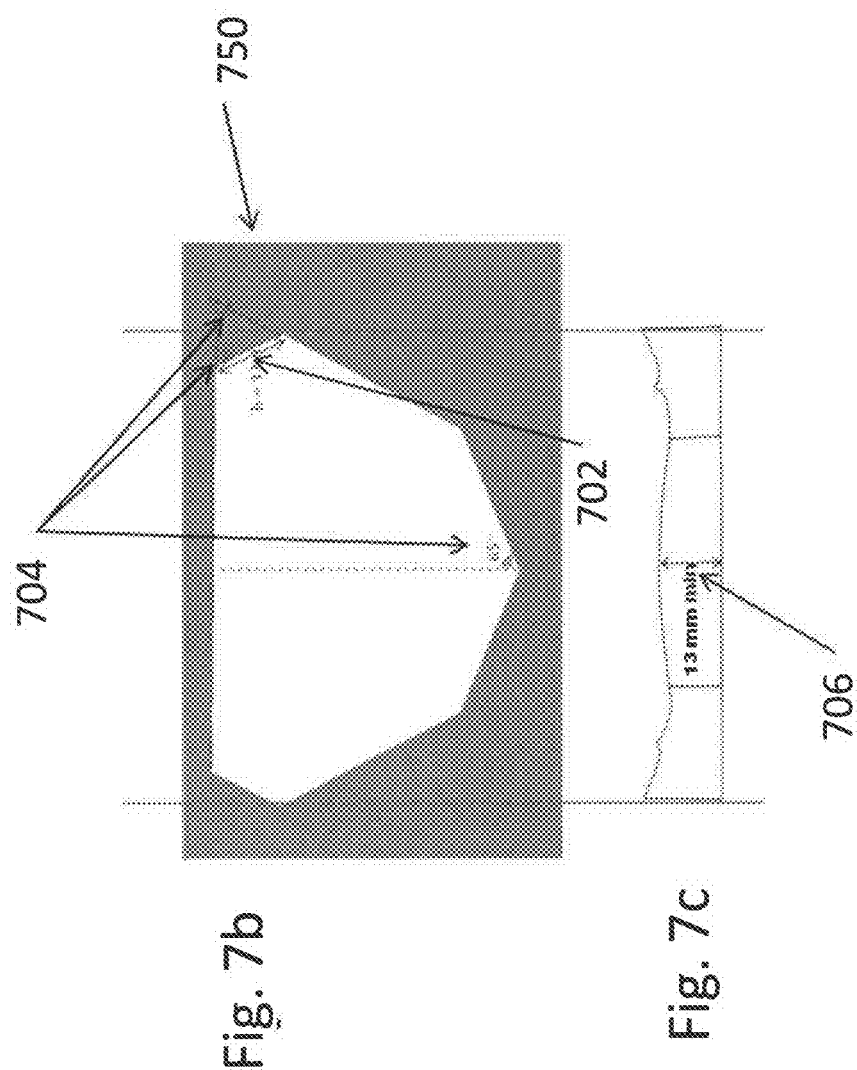

FIG. 7b is a diagram that shows a top view of an exemplary footprint for a virtual dental base model embodiment (e.g., maxillary arch) according to the application. FIG. 7c is a diagram that shows a cross-sectional view of an exemplary virtual dental base model embodiment in FIG. 7b according to the application. As shown in FIG. 7b, an oblique face 702 of a virtual base 750 has a prescribed length and selected angles 704 have a prescribed arc. As shown in FIG. 7c, upper portion 750 (or lower portion 760) of the virtual base 700 is higher than a prescribed height 706 (e.g., minimum height).

FIG. 7c is a diagram that shows a perspective view of an exemplary virtual dental base model embodiment (e.g., maxillary arch and/or mandibular arch) according to the application. As shown in FIG. 7c, a distance 708 between the lower and/or upper portions 750, 760 is between a prescribed range.

Figures 7D, 7E:
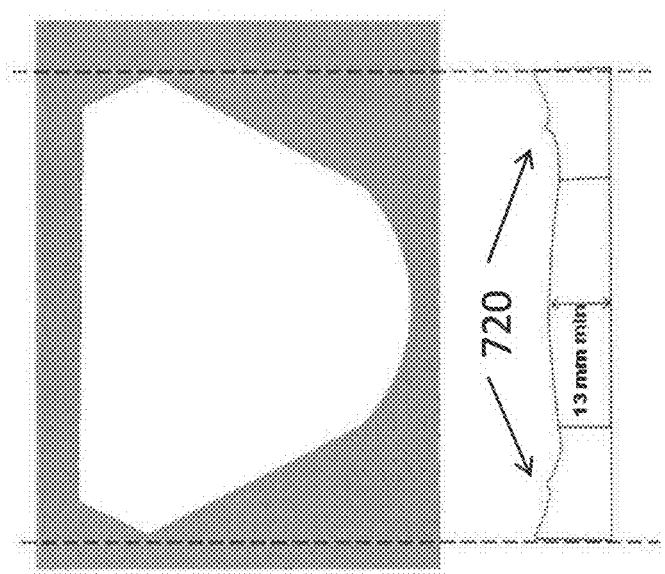

FIG. 7d is a diagram that shows a top view of an exemplary footprint for a virtual dental base model embodiment (e.g., mandibular arch) according to the application. FIG. 7e is a diagram that shows a cross-sectional view of an exemplary virtual dental base model embodiment (e.g., mandibular arch) according to the application. As shown in FIG. 7d, an oblique face 702 of a virtual base 700 has a prescribed length and selected angles 704 have a prescribed arc. As shown in FIG. 7c, lower and/or upper portions 750, 760 of the virtual base 700 are higher than a prescribed height 706. In the exemplary embodiment of FIG. 7d, the mandibular base 760 can have the same rules as the maxillary base, but can have a curved shaped (e.g., a circle shape) in the front. In one embodiment, angle 704 can be 65 degrees, a prescribed height threshold 706 can be 13 mm, and length 702 can be 13 mm.

The dental frenum (or frenulum) is a small fold of skin between the lip and the gum. In certain exemplary embodiments, the frenulums can be represented as small peaks on the surface of the virtual base. As shown in FIGS. 7a-7e, on the right and left sides of the base, we can see the dental frenulum 720, In one embodiment, angle 704 can be 65 degrees and length 702 can be 1.3 mm.

An obtain teeth 3-D model step S610 then inputs 3-D digital model of the patient's dentition. As described herein, the 3-D digital model of the patient's dentition can be obtained as known to one skilled in the art (e.g., using extraoral or intraoral techniques). A determine bounding dimensions of the 3-D digital model of the patient's dentition step S620 can determine a 3-D enclosure surrounding the 3-D digital model of the patient's dentition. As shown in FIG. 8, a 3-D bounding box 810 is determined to surround a 3-D digital model 820 of the patient's dentition. In FIG. 8, the bounding box 810 is illustrated as a 2D rectangle with dimensions to surround both the upper and lower dental arch models. In certain exemplary embodiments, the bounding box 810 can surround the upper and lower dental arch models that are in an occlusal position or relationship.

Figure 9:
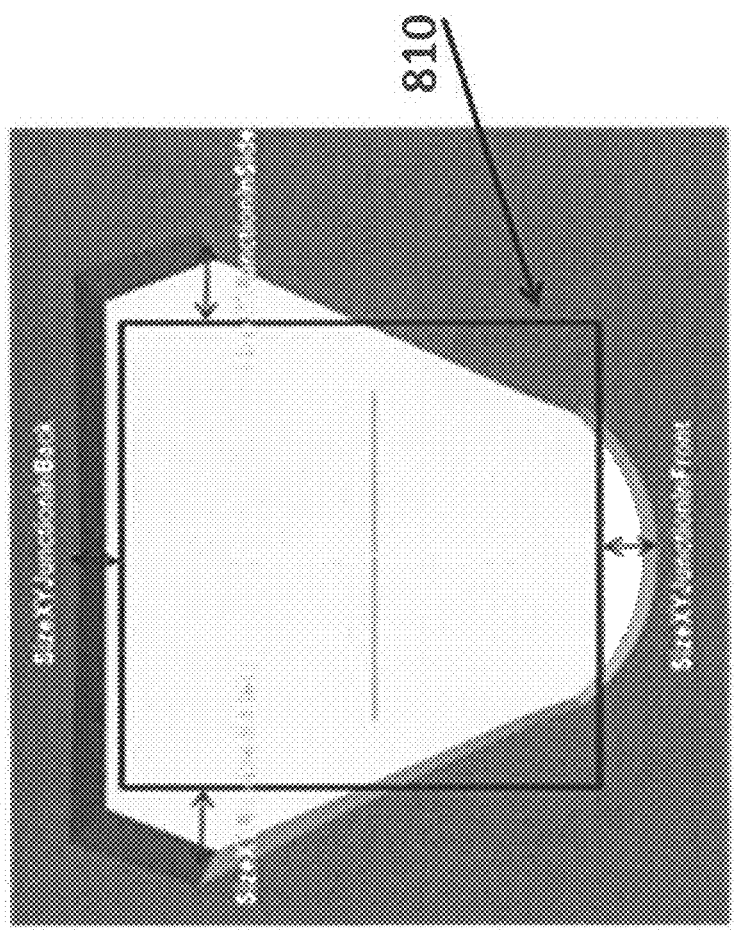
FIG. 9 is a diagram that shows exemplary sizing applied to a virtual base model embodiment.

A transformation step S630 can then preferably automatically generate virtual base model. In certain exemplary embodiments, the transformation step S630 can include global and local transformations based on bounding dimensions and local criteria. The dimensions of the maxillary and mandibular bases (e.g., height and length of the faces as well as the total height of both models 750, 760 put together in occlusion (and optionally a position of the frenulums), are preferably automatically adapted to the size and shape of the maxillary and mandibular reconstructed virtual teeth models. As shown in FIG. 9, from the 3D bounding box 810 of the global teeth model (e.g., maxillary and mandibular), an initial desired or optimal size can be determined for the virtual base(s) 750, 760. The initial virtual base size can then undergo global transformations adjusting the virtual base as a whole.

Figure 10:
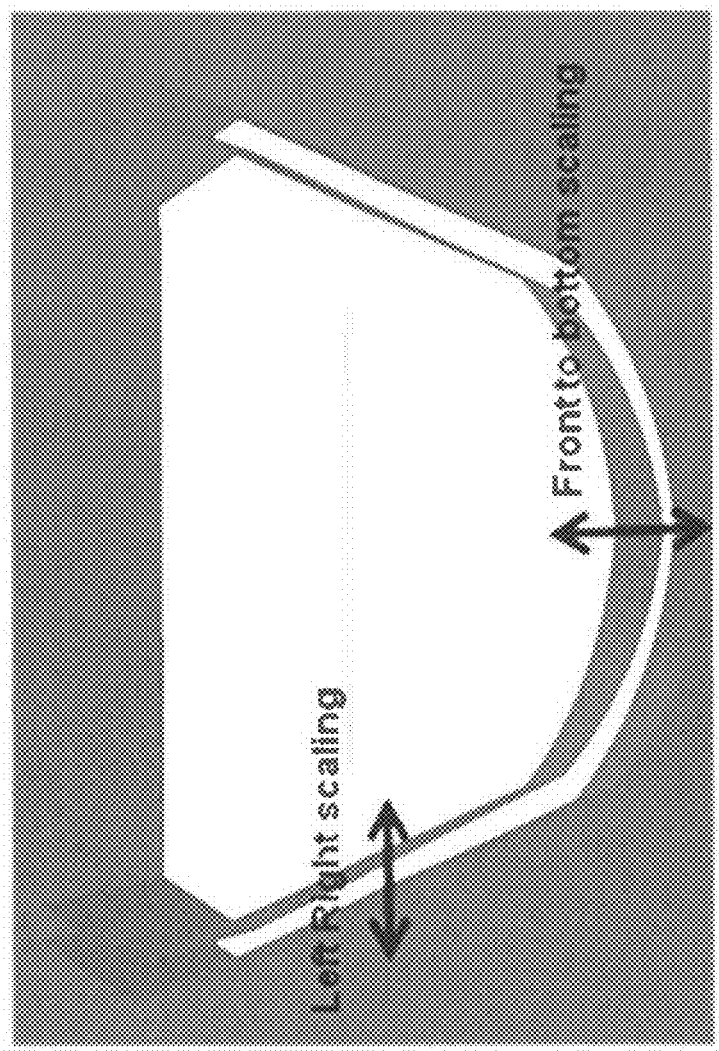
FIG. 10 is a diagram that shows exemplary global transformations applied to a virtual base model embodiment.
Figure 11:
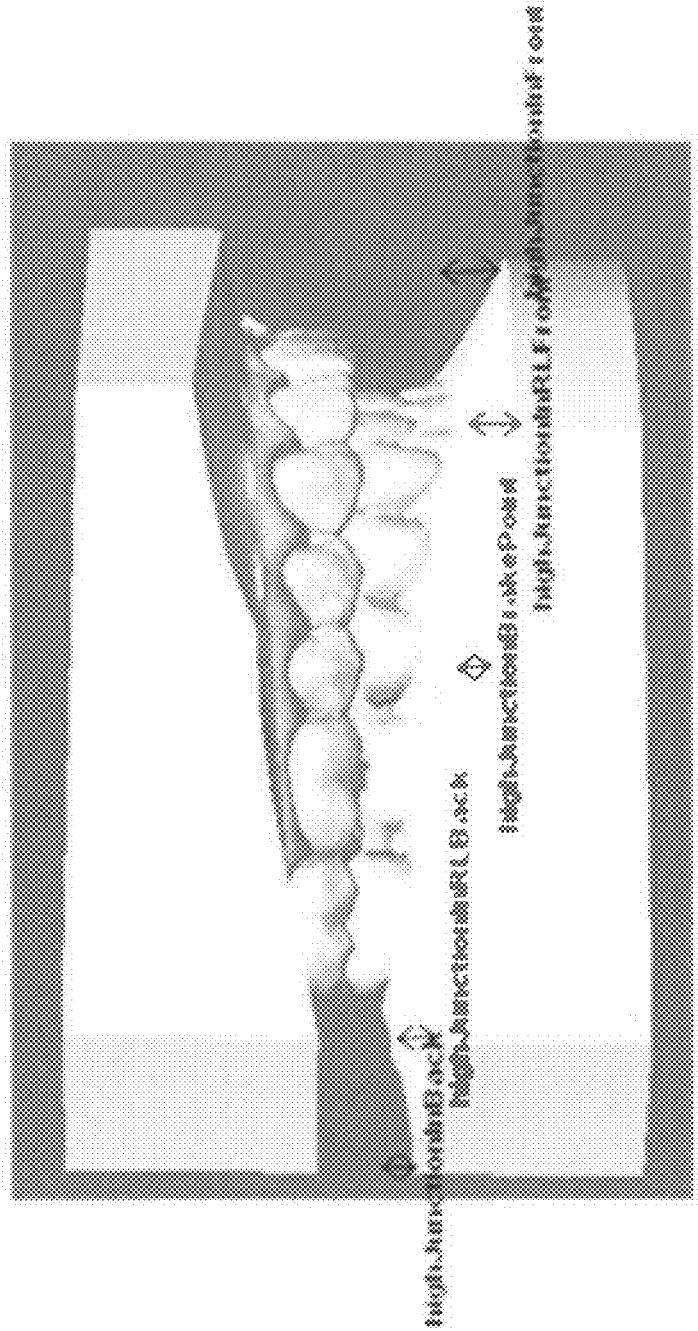
FIG. 11 is a diagram that shows an exemplary local transformations applied to a virtual base model embodiment.

Global transformations provided by certain exemplary embodiments include (i) translation of the faces to be placed at the optimal distance (e.g., required height) and/or (ii) global scaling from front to bottom and from right to left. FIG. 10 is a diagram that illustrates exemplary global transformations applied to an initially sized virtual base model. In one exemplary embodiment, an initial virtual base(s) can be automatically deformed to have the selected size that corresponds to current aesthetic criteria and/or to a current practice for the definition of the model base of the real plasters of patient teeth. In alternate exemplary embodiments, some manual input can also be contemplated or used. In step S730, the globally transformed virtual base model can then undergo local transformations. In one embodiment, exemplary local transformations can be performed section by section (e.g., rear sides, middle sides and front sides, Local transformations provided by certain exemplary embodiments include local movement of the main or primary points of the virtual base (e.g., corner, front points, frenulums, etc). FIG. 11 is a diagram that illustrates exemplary local transformations applied to a globally transformed virtual base model. As shown in FIG. 11, for each section, the height of the globally transformed base can then be locally adapted, by changing the local height of the base along the illustrated arrows.

A display step S630 can then preferably display a final virtual base model assembled with the virtual teeth model. The final virtual base models according to exemplary method and/or apparatus embodiments of the application still maintain the prescribed requirements (e.g., respect the norms of the ABO defined requirements. The final virtual base model can alternatively be stored or transmitted for use.

Figure 12:
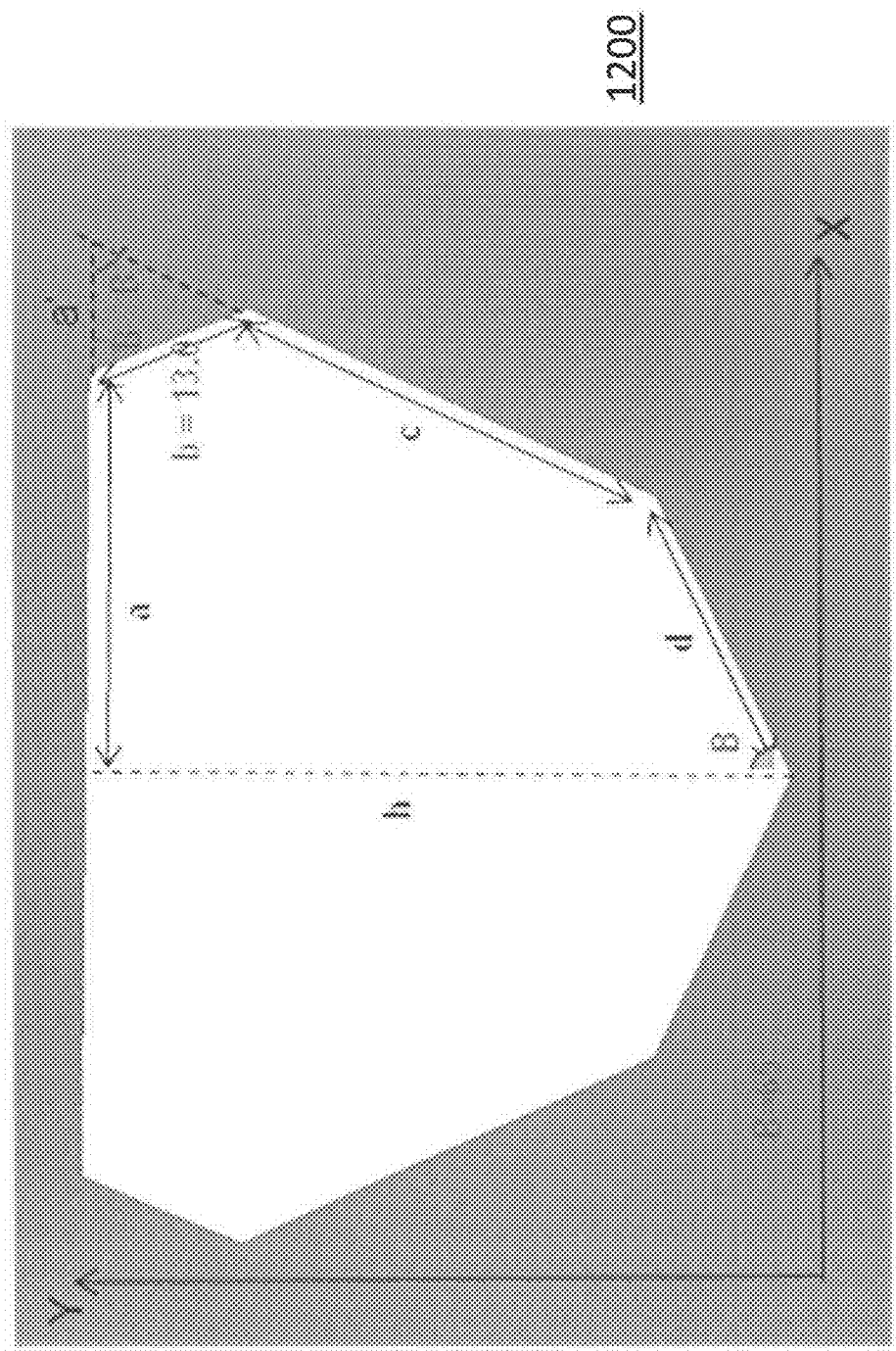
FIG. 12 is a diagram that shows exemplary parameters for a virtual base model determination embodiment.

Exemplary Definition of the Parametric Virtual Base:

Exemplary parameters for a virtual base model determination embodiment are illustrated in FIG. 12. In one exemplary process embodiment, a virtual dynamic base 1200 can be determined, entirely parametrically, with the following algorithmic relationship shown in equation (1):

$$d=[(a+a')\tan \beta - h]/q$$

$$c=(a+a')/q+h*[1/\sin \beta - 1/(q*\tan \beta)]-b \quad \text{Equation (1)}$$

where:

$$q=\sin \beta \tan \beta - \cos \beta$$

$$a'=b*\text{sqrt}(2-2\cos \beta))$$

If a scale is applied to the virtual dynamic base 1200 (e.g., scale value in $X=S_a$ and scale value in $Y=S_h$), then the various length change as following equation (2):

$$\Delta a=(S_a-1.0)*a$$

$$\Delta b=0.0$$

$$\Delta_h=(S_h-1.0)*h$$

$$\Delta_d=\Delta a*\tan \beta/q - \Delta_h/q$$

$$\Delta_c=\sqrt{[\Delta_d*\Delta_d+\Delta_h*\Delta_h-2*\Delta_d*\Delta_h*\cos \beta]} \quad \text{Equation (2)}$$

Figure 13:
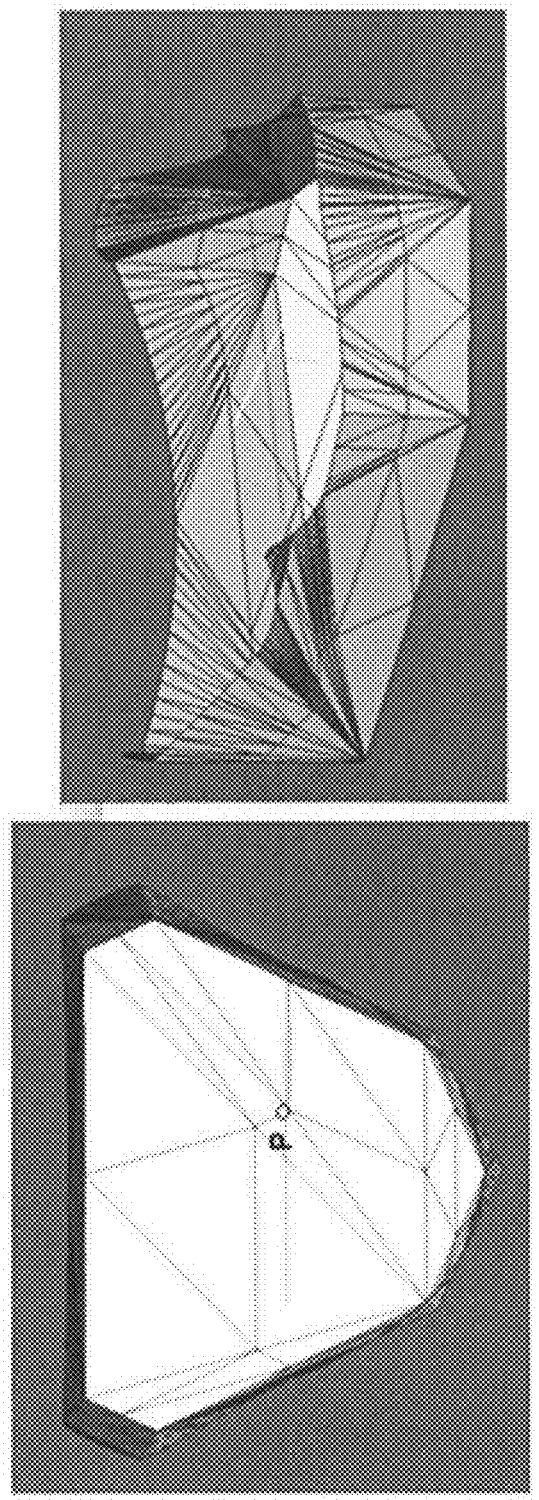
FIG. 13 is a diagram that shows an exemplary virtual base model comprising a polygonal mesh.

Preferably, the virtual base model is not a uniform mesh. In certain exemplary embodiments, the virtual base model 1200 contains some points and triangles. FIG. 13 is a diagram that illustrates an exemplary polygonal (e.g., triangular) mesh forming the virtual base model 1200.

For each point of the base P ($P_x$, $P_y$, $P_z$), as shown in FIG. 13, a position can be defined, which depends only of a, h, c, d, h and β, and so only depends on a, h, b and β (because c and d depends only on a, h, b and β). When the scale is applied, then the new position of the point P is the following equation (3):

$$P'=P+w_a*\Delta_a X+w_c*\Delta_c V_c+w_d*\Delta_d*V_d \quad \text{Equation (3)}$$

If (Py>−b*sin β)
$w_c=0.0$ and $w_d=0.0$
If (−(b+c)*sin β<Py<−b*sin β)
$w_d=0.0$
If (Py<−(b+c)*sin β)
$w_c=1.0$ The vector $V_d$ and $V_c$ are different if Px is positive or negative. Accordingly, a deformation of each point on a virtual base model according to the deformation (e.g., global or local) applied on the base can be determined.

FIG. 14 is a diagram that illustrates local movements along an exemplary virtual base model embodiment. As shown in FIG. 14, for the local movements (e.g., local z scale and local xy displacement), xy local displacement can be done only along the segment where the point is positioned. For example, if P belongs to the front right edge, then it can be moved only along the vector $V_d$. For the local z scale: a point belonging to a vertical face can be moved according to its distance to the associated edge and bottom points.

Certain exemplary method and/or apparatus embodiments according to the application can provide virtual definition of the base of a dental virtual mode. Exemplary embodiments according to the application can include various features described herein (individually or in combination). Exemplary method embodiments shown in FIG. 6 can be can be performed by standalone computers, workstations or the like, or the same or control logic processors integral to dental imaging apparatus/dental x-ray systems; however, method embodiments of FIG. 6 is not intended to be limited thereby.

In certain exemplary embodiments, parameters for a virtual base model determination such as determined by equations (1)-(3) can be used to implement step S630 in whole or in part; however, method embodiments of FIG. 6 is not intended to be limited thereby.

Certain exemplary embodiments can provide formation of individualized digital model bases for each patient from a plurality of prescribed dimensions and hounding dimensions of a 3-D digital model of said each patient's dentition. Certain exemplary method and/or apparatus embodiments can provide formation of personalized digital model bases for each patient (e.g., dentition models) that remain compliant with ABO regulations and/or promulgated regulatory agency requirements.

Consistent with one embodiment of the present disclosure, the present disclosure utilizes a computer program with stored instructions that perform on image data accessed from an electronic memory. As can be appreciated by those skilled in the image processing arts, a computer program of an embodiment of the application can be utilized by a suitable, general-purpose computer system, such as a personal computer or workstation. However, many other types of computer systems can be used to execute the computer program of the application, including networked processors. The computer program for performing the method of the application may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the application may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the application may make use of various image manipulation algorithms and processes that are well known. It will be further understood that the computer program product embodiment of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware components and elements known in the art.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A computer-implemented method for generating a digital model base from a digital model of a patient's dentition, the method comprising:

forming an initial virtual base from a plurality of prescribed dimensions of a selected virtual base type;

obtaining a 3-D digital model of the patient's dentition;
determining bounding dimensions of the 3-D digital model of the patient's dentition;
performing a first translation of the initial virtual base based on the bounding dimensions;
performing a second translation of the translated virtual base based on local criteria to form the digital model base; and
displaying, storing or transmitting the digital model base.

2. The method of claim 1, wherein the selected virtual base type is a regulated virtual base type or complies with the American Board of Orthodontics regulations.

3. The method of claim 1, wherein the bounding dimensions include a 3-D bounding box of at least one of portions of an upper dental arch, portions of a lower dental arch, or both the upper dental arch and the lower dental arch in occlusion.

4. The method of claim 1, wherein the digital model base comprises an upper virtual base and further comprises a lower virtual base, and wherein the plurality of prescribed dimensions of a selected virtual base type include (i) length of an oblique face of at least one pair of sides comprising a rear corner side, (ii) an angle of the rear corner side to a back side, (iii) an angle between one side of a second pair of sides comprising a front side and an orthogonal line from the back side; a range of height encompassing the distance from a top surface of the upper virtual base to a bottom surface of the lower virtual base, and a height limit of the upper virtual base and the lower virtual base.

5. The method of claim 1, wherein the first translation of the initial virtual base comprises a global translation of the initial virtual base scaled from front to back depth dimension and a left to right width dimension.

6. The method of claim 1, wherein the digital model base comprises an upper virtual base including a perimeter formed of a back side, a pair of oblique rear sides at opposite ends of the back side, a pair of front sides opposing the back side, and a pair of middle sides connecting the front sides to the rear sides.

7. The method of claim 1, wherein the digital model base comprises a lower virtual base having a perimeter formed of a back side, a pair of oblique rear sides at opposite ends of the back side, a pair of middle sides opposing the back side and respectively connected at a first end of each of the middle sides to a respective oblique rear side, and a front curved side respectively connected to a second end of each of the middle sides, where the front curved side comprises an arc of a circle.

8. The method of claim 1, wherein the local criteria of the second translation of the translated virtual base comprise local movement of selected points on each of rear sides, middle sides and front sides of the virtual base.

9. The method of claim 1, wherein the digital model base comprises an upper virtual base or a lower virtual base, and wherein a dental frenulum is represented on the digital model base.

10. The method of claim 1, wherein an operator instruction can adjust a portion of the digital model base.

11. The method of claim 1, further comprising a step of adjusting each point of the surface of the virtual model base according to z scale displacement and local xy displacement.

* * * * *